US009819138B2

(12) United States Patent
Ichihara (10) Patent No.: US 9,819,138 B2
(45) Date of Patent: Nov. 14, 2017

(54) OBJECT INFORMATION ACQUIRING APPARATUS, LASER APPARATUS, AND MEDICAL APPARATUS

(71) Applicant: CANON KABUSHIKI KAISHA, Tokyo (JP)

(72) Inventor: Shigeru Ichihara, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 144 days.

(21) Appl. No.: 14/341,081

(22) Filed: Jul. 25, 2014

(65) Prior Publication Data
US 2015/0045778 A1 Feb. 12, 2015

(30) Foreign Application Priority Data

Aug. 6, 2013 (JP) .................................. 2013-162941

(51) Int. Cl.
*H01S 3/13* (2006.01)
*H01S 3/092* (2006.01)
(Continued)

(52) U.S. Cl.
CPC .............. *H01S 3/092* (2013.01); *A61N 5/062* (2013.01); *G01N 29/0654* (2013.01);
(Continued)

(58) Field of Classification Search
CPC ........ H01S 3/092; H01S 3/091; H01S 3/0912; H01S 3/13; H01S 3/1305; H01S 3/1306; H01S 3/1312; H01S 3/11
(Continued)

(56) References Cited

U.S. PATENT DOCUMENTS 4,829,530 A * 5/1989 Sato ........................ H01S 3/092
372/33
6,355,905 B1 3/2002 Sasaki et al. ............ 219/121.62
(Continued)

FOREIGN PATENT DOCUMENTS

JP H07-022676 1/1995
JP H11-214775 8/1999
(Continued)

OTHER PUBLICATIONS

U.S. Appl. No. 14/321,891, filed Jul. 2, 2014.
Office Action dated Apr. 25, 2017 in counterpart Japanese patent application 2013-162941, with machine translation.

*Primary Examiner* — Kinam Park
(74) *Attorney, Agent, or Firm* — Fitzpatrick, Cella, Harper & Scinto (57) ABSTRACT

An object information acquiring apparatus is used which includes a laser medium that oscillates laser light, an excitation source that excites the laser medium, a voltage accumulator that applies a voltage to the excitation source, a voltage supplier that supplies a voltage to the voltage accumulator, a voltage controller that limits a maximum supplied voltage from the voltage supplier, a receiver that receives a photoacoustic wave generated by an object irradiated with the laser light, and a constructor that acquires characteristic information relating to the object in use of the photoacoustic wave, wherein the voltage controller compares a measured voltage value obtained by implementing division of a supplied voltage from the voltage supplier with a reference voltage value defining the maximum supplied voltage.

20 Claims, 6 Drawing Sheets (51) Int. Cl.
*G01N 29/24* (2006.01)
*H01S 3/11* (2006.01)
*H01S 3/131* (2006.01)
*H01S 3/102* (2006.01)
*A61N 5/06* (2006.01)
*G01N 29/06* (2006.01)
*G01N 29/44* (2006.01)
*A61B 18/20* (2006.01)
*A61N 5/067* (2006.01)
*A61B 18/00* (2006.01)
*A61B 5/00* (2006.01)
*H01S 3/091* (2006.01)
*H01S 3/10* (2006.01)

(52) U.S. Cl.
CPC ..... *G01N 29/2418* (2013.01); *G01N 29/4436* (2013.01); *H01S 3/1022* (2013.01); *H01S 3/11* (2013.01); *H01S 3/13* (2013.01); *H01S 3/1305* (2013.01); *H01S 3/1306* (2013.01); *H01S 3/1312* (2013.01); *A61B 5/0095* (2013.01); *A61B 18/20* (2013.01); *A61B 2018/00642* (2013.01); *A61B 2018/00767* (2013.01); *A61N 2005/067* (2013.01); *A61N 2005/0626* (2013.01); *H01S 3/0912* (2013.01); *H01S 3/10069* (2013.01)

(58) Field of Classification Search
USPC .................................................. 372/70, 30
See application file for complete search history.

(56) References Cited

U.S. PATENT DOCUMENTS

| | | | |
|---|---|---|---|
| 8,761,225 B2* | 6/2014 | Ichihara | H01S 3/091 372/29.011 |
| 2003/0156615 A1* | 8/2003 | Kennedy | H01S 3/115 372/55 |
| 2010/0043526 A1* | 2/2010 | Helwegen | G01N 21/1702 73/24.02 |
| 2013/0070802 A1 | 3/2013 | Ichihara | 372/70 |
| 2014/0031667 A1 | 1/2014 | Ichihara et al. | 600/407 |
| 2014/0092932 A1 | 4/2014 | Ichihara | 372/100 |
| 2014/0109678 A1* | 4/2014 | Ichihara | H01S 3/092 73/655 |
| 2014/0123762 A1 | 5/2014 | Furukawa et al. | 73/655 |
| 2014/0148660 A1 | 5/2014 | Irisawa et al. | 600/309 |
| 2014/0185634 A1 | 7/2014 | Ichihara et al. | 372/10 |

FOREIGN PATENT DOCUMENTS

| | | |
|---|---|---|
| JP | 11-284284 A | 10/1999 |
| JP | 2000-135579 | 5/2000 |
| JP | 2013-004851 | 1/2013 |
| JP | 2013-051406 | 3/2013 |

* cited by examiner

OBJECT INFORMATION ACQUIRING APPARATUS, LASER APPARATUS, AND MEDICAL APPARATUS

BACKGROUND OF THE INVENTION

Field of the Invention

The present invention relates to an object information acquiring apparatus, a laser apparatus, and a medical apparatus.

Description of the Related Art

Lasers are utilized for a variety of applications such as industrial machining apparatuses, manufacturing apparatuses for semiconductor equipment, and treatment and diagnosis apparatuses for medical equipment. In recent years, solid lasers such as semiconductor lasers and fiber lasers have been significantly improved in characteristics. On the other hand, flash lamp pumped lasers are available as lasers particularly suitable for cosmetic and medical equipment for, for example skin treatment.

Flash lamp pumped solid lasers are characterized by providing high oscillation output per pulse. However, disadvantageously, degradation of a flash lamp may lead to an unstable laser output such as a reduced laser output.

An oscillation output from the laser varies according to the emission strength of the flash lamp, which depends on a voltage applied to the flash lamp. Japanese Patent Application Laid-open No. H11-284284 discloses a technique intended to stabilize the laser oscillation output by measuring the output value of emitted laser light and adjusting the voltage applied to the flash lamp in accordance with the output value.

Patent Literature 1: Japanese Patent Application Laid-open No. H11-284284

SUMMARY OF THE INVENTION

The thermal energy of light emission from the flash lamp significantly affects the stability of a laser resonator. Thus, a laser apparatus is designed and aligned in consideration for the thermal energy so as to suppress resonator loss and to maximize oscillation efficiency. In this case, the laser output can be controlled by adjusting the voltage applied to the flash lamp in accordance with increase and decrease in laser output, as disclosed in Japanese Patent Application Laid-open No. H11-284284.

However, the laser output decreases when the condition of the laser is changed from its initial condition as a result of misalignment of the resonator or a change in installation environment. In this state, an increase in output based on the control of the applied voltage may impose a load on the laser apparatus, leading to a shortened life of the apparatus. This disadvantageously makes stabilization of the laser apparatus difficult.

With the above-described problems in view, it is an object of the present invention to identify more easily the condition of the laser apparatus to improve the controllability of the laser apparatus by adjusting the output from the laser apparatus within a needed range, thus allowing the laser apparatus to be stably utilized.

The present invention provides an object information acquiring apparatus comprising:
a laser medium that oscillates laser light;
an excitation source that excites the laser medium;
a voltage accumulator that applies a voltage to the excitation source;
a voltage supplier that supplies a voltage to the voltage accumulator;
a voltage controller that limits a maximum supplied voltage from the voltage supplier;
a receiver that receives a photoacoustic wave generated by an object irradiated with the laser light; and
a constructor that acquires characteristic information relating to the object in use of the photoacoustic wave,
wherein the voltage controller compares a measured voltage value obtained by implementing division of a supplied voltage from the voltage supplier with a reference voltage value defining the maximum supplied voltage.

The present invention also provides a laser apparatus comprising:
a laser medium that oscillates laser light;
an excitation source that excites the laser medium;
a voltage accumulator that applies a voltage to the excitation source;
a voltage supplier that supplies a voltage to the voltage accumulator; and
a voltage controller that limits a maximum supplied voltage from the voltage supplier;
wherein the voltage controller compares a measured voltage value obtained by implementing division of a supplied voltage from the voltage supplier with a reference voltage value defining the maximum supplied voltage.

The present invention enables the condition of the laser apparatus to be identified more easily so as to improve the controllability of the laser apparatus by adjusting the output from the laser apparatus within a needed range, thus allowing the laser apparatus to be stably utilized.

Further features of the present invention will become apparent from the following description of exemplary embodiments with reference to the attached drawings.

DESCRIPTION OF THE EMBODIMENTS

Preferred embodiments of the present invention will be described below with reference to the drawings. However, the dimensions, materials, shapes, and relative arrangement of components described below should be appropriately changed depending on a configuration of an apparatus to which the present invention is applied or various other conditions, and are not intended to limit the scope of the present invention to the description below.

The present invention is applicable to, for example, an apparatus that generates laser light and a medical apparatus, a diagnosis apparatus, and an object information acquiring apparatus all of which use the laser apparatus. The object information acquiring apparatus includes an apparatus that receives a photoacoustic wave generated, under a photoacoustic effect, in an object irradiated with light (electromagnetic wave) to acquire characteristic information as object information in the form of image data. The characteristic information acquired is indicative of the distribution of sources of acoustic waves resulting from light irradiation, the distribution of initial sound pressure in the object, or the distribution of light energy absorption density or absorption coefficient derived from the distribution of initial sound pressure, or the distribution of concentrations of substances forming the tissue. The distribution of concentrations of substances is represented by, for example, the distribution of oxygen saturation or the distribution of concentrations of oxidized/reduced hemoglobin.

The term "acoustic wave" as used herein typically refers to an ultrasound wave and includes an elastic wave referred to as a sound wave, an ultrasound wave, or an acoustic wave. An acoustic wave resulting from the photoacoustic effect is referred to as a photoacoustic wave.

Embodiment 1

Embodiment 1 of the present invention will be described.
<Apparatus Configuration>
A configuration of a laser apparatus according to Embodiment 1 will be described with reference to a schematic diagram in FIG. 1.

A laser apparatus includes a power supplier 101, a laser oscillator 102, a laser controller 103, a laser operator 104, and a display 105.

The power supplier 101 has a voltage supplier 106 and a voltage accumulator 107. A laser oscillator 102 includes an excitation vessel 110 including an excitation source 108 and a laser medium 109, and a resonator 111 including a reflection mirror and an exit mirror. The laser operator 104 allows the voltage supplier 106 to supply a voltage to the voltage accumulator 107 via the laser controller 103 to apply electric energy to the excitation source 108. The excitation source 108 excites the laser medium 109 to generate fluorescence, and the resonator 111 including the reflection mirror and the exit mirror amplifies the light intensity of the fluorescence, causing laser oscillation.

The type of the laser apparatus depends on the configuration of the laser oscillator including the excitation source 108, the laser medium 109, and the resonator 111.

A flash lamp pumped solid laser using a flash lamp as the excitation source 108 is a form of the laser apparatus according to the present invention. Efficient excitation can be achieved by matching the waveform of emission pulses from the flash lamp with the upper-level fluorescence lifetime of the laser medium 109 contributing to laser oscillation.

The voltage accumulator 107 includes a pulse forming network (PFN). The waveform of emission pulses from the flash lamp can be adjusted by optimizing a coil and a capacitor both providing the PFN. The laser medium 109 having a long upper-level fluorescence lifetime is preferable for flash lamp excitation. For example, the laser medium 109 is formed of YAG (Yttrium Aluminum Garnet) which serves as a base material crystal and to which Nd, Ho, Cr, Tm, or the like is added or of chrysoberyl which serves as a base material crystal and to which Cr is added.

The flash lamp emits light based on arc discharge using xenon or krypton gas. The emission strength of the flash lamp depends on a voltage supplied by the voltage supplier 106 and electric energy based on the coil capacity of the PFN. Thus, a high emission intensity can be easily achieved. However, the flash lamp has a wide emission band and thus inefficiently utilizes energy in connection with excitation of the laser medium. Most of the emission energy fails to be converted into laser output and dissipates as thermal energy. It is important to design the resonator in consideration for thermal energy to stabilize laser oscillation.

As another laser apparatus according to the present invention, a laser irradiation source may be used as the excitation source 108. For example, the laser irradiation source may be a titanium sapphire (Ti:sa) laser that is a wavelength variable laser capable of providing oscillation over a wide band. A Ti:sa crystal has a short upper-level fluorescence lifetime and thus oscillates inefficiently when directly excited by a flash lamp. Thus, the Ti:sa crystal is put to practical use by increasing the oscillation efficiency using the second harmonic of a flash lamp pumped Nd:YAG laser as a seed light source.

Moreover, a diode pumped solid state laser (DPSS laser) using a semiconductor laser as an excitation source is a laser suitable for the present invention. An example of a preferred laser medium is Nd:YVO4 containing YVO4 (Yttrium Vanadate) as a mother crystal. Other examples include Nd:YAG, Yb:YAG, and Nd:GdVO4 (Nd Doped Dadolinium Orthovanadate).

The power supplier 101 has a voltage controller 112 that limits the maximum supplied voltage supplied by the voltage supplier 106. The voltage controller 112 directly controls the supplied voltage output by the voltage supplier 106. The present invention can be carried out even in a configuration in which the voltage controller 112 is included in the laser controller 103 or operates under the control of the laser controller 103.

In the configuration according to Embodiment 1, the display 105 shows a measured voltage value and a reference voltage value both illustrated in control steps described below and executed by the voltage controller 112.

Figure 2:
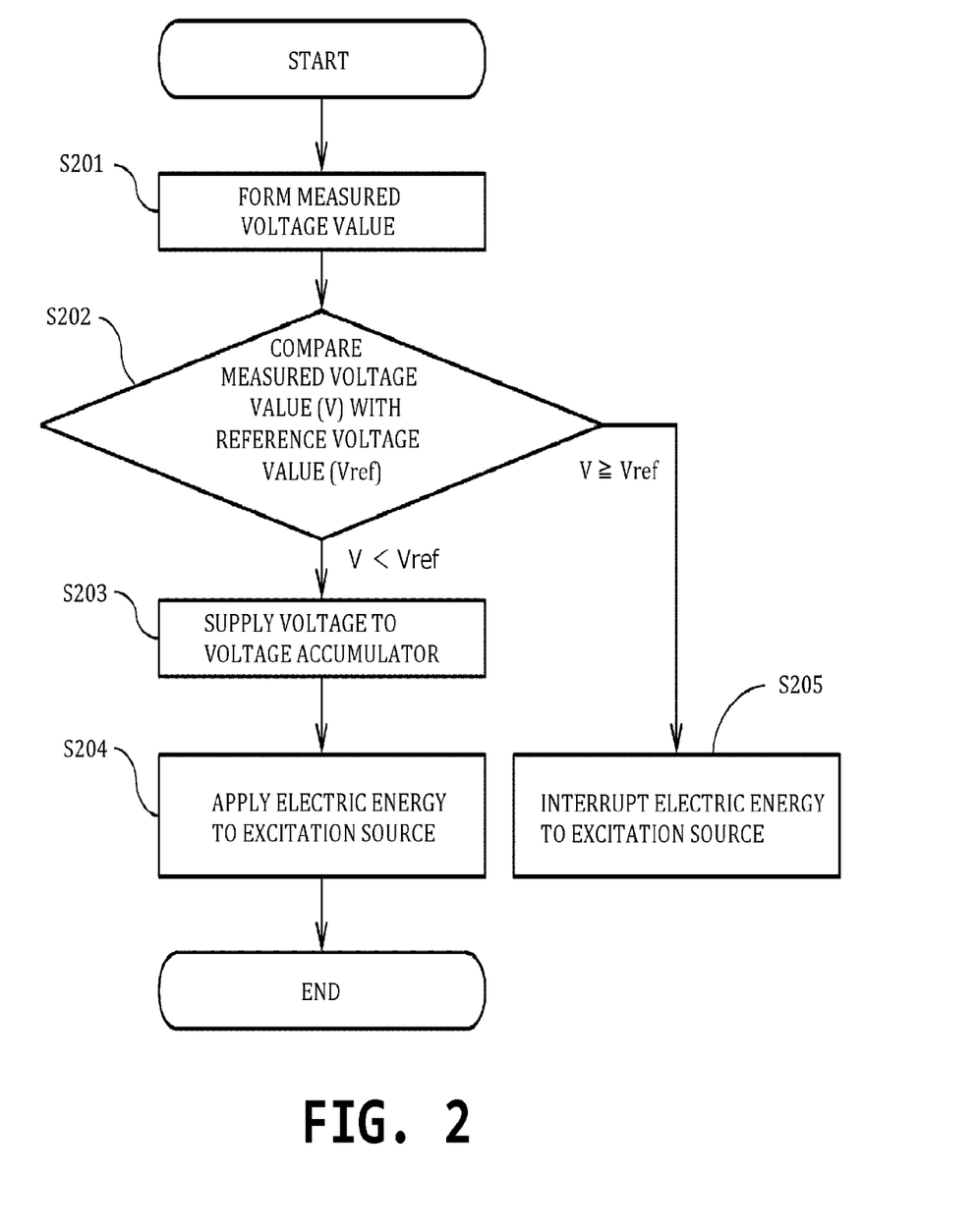
FIG. 2 is a flowchart showing control steps according to the present invention.

<Control Steps>
The control steps will be described using a flowchart in FIG. 2.

"Step S201 (Formation of a Measured Voltage Value)"
In step S201, the voltage controller 112 measures a voltage supplied to the voltage accumulator 107 by the voltage supplier 106, by implementing division of the voltage. The measured value is hereinafter referred to as a measured voltage value (V). When the supplied voltage is approximately 1 kV, approximately one two-hundredths of the supplied voltage is determined to be the measured voltage value. The measured voltage value is formed by implementing voltage division depending on the supplied voltage and a comparator succeeding the voltage controller 112, and is not limited to one two-hundredths of the supplied voltage.

"Step S202 (Comparison between the Measured Voltage Value and the Reference Voltage Value)"
In step S202, the comparator circuit is used to compare the measured voltage value (V) with a reference voltage value (Vref) defining the preset maximum allowable value of the supplied voltage.

"Step S203 (Voltage Supplied to the Voltage Accumulator)"
In step S203, when the measured voltage value is lower than the reference voltage value (V<Vref) based on the result of the comparison in step S202, the voltage is supplied to the voltage accumulator 107.

"Step S204 (Application of Electric Energy)"
In step S204, electric energy is applied to the flash lamp, which serves as the excitation source 108.

"Step S205 (Interruption of Electric Energy)"

In step S205, when, in step S202, the measured voltage value is equal to or higher than the reference voltage value (V≥Vref), the application of electric energy to the excitation source 108 is interrupted.

<Effects>

The flash lamp pumped solid laser can be put to practical use by increasing the applied voltage in keeping with degradation of the flash lamp to adjust the laser output. In this case, the above-described control steps enable the laser output to be adjusted within a preset output range.

In particular, with the degradation of the flash lamp being gradual, if the maximum supplied voltage, which is defined by the reference voltage value, is pre-limited, it becomes possible to identify the laser condition, whereby a state of the laser exhibiting no significant change can be determined to be a range at which stable use is enabled. Furthermore, advantageously, constant display of the measured voltage value and the reference voltage value serves as an indicator for the exhaustion state of the flash lamp.

On the other hand, for the flash lamp pumped solid laser, the laser output is stabilized when the thermal energy of the flash lamp allows the thermal state around the resonator to reach an equilibrium state. Hence, if the output decreases slightly depending on the thermal state when the laser starts oscillating, the applied voltage is controlled to adjust the output. However, when the applied voltage is excessively adjusted while transient laser oscillation is unstable, not only the stability of the laser is impaired but also a load is imposed on the laser apparatus, leading to a shortened life of the laser apparatus or the like.

Figure 1:
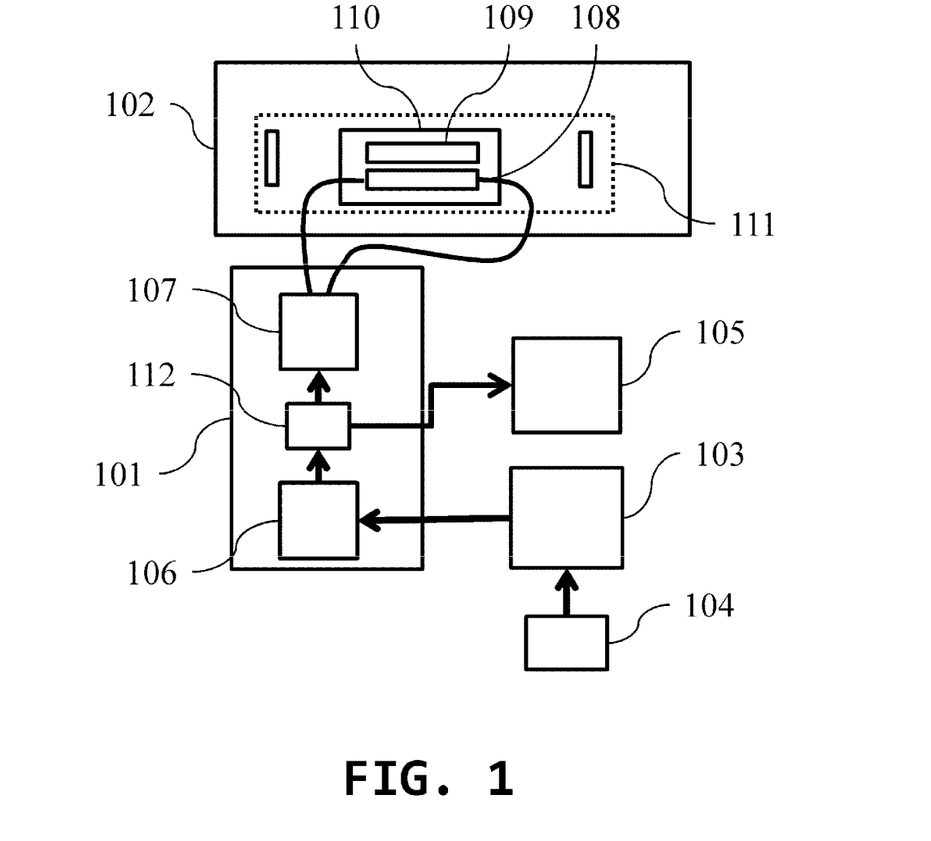
FIG. 1 is a schematic diagram showing an embodiment of a laser apparatus according to the present invention.

Thus, excessive output adjustment can be suppressed by using the laser apparatus with the voltage controller 112 according to the present invention shown in FIG. 1. Then, the laser condition can be understood to allow the laser apparatus to be stably used. Furthermore, constant display of the measured voltage value and the reference voltage value enables an oscillation output state to be constantly monitored. The comparison result need not necessarily be displayed for output adjustment but an information processing may perform relevant control using the comparison result.

<Variation>

In a preferred aspect, the display 105 in FIG. 1 not only directly shows the measured voltage value and reference voltage value related to the comparison result but also shows the ratio of the measured voltage value to the reference voltage value. The display of the ratio allows the laser output with respect to a preset maximum allowable laser output to be easily understood.

Moreover, in a preferred aspect, the ratio is used within a given range. When the ratio utilized is lower than 100% and equal to or higher than 90%, the laser is likely to be used with the appropriate range of output adjustment maintained. When the ratio is lower than 90%, the controllable range of the output is wide and the object of the present invention often fails to be accomplished, depending on the laser configuration. On the other hand, setting the ratio to 95% or higher further improves the stability of the laser. However, it should be noted that an extremely narrow range of output adjustment frequently makes the supplied voltage close to the maximum value, imparting the convenience of the adjustment.

Embodiment 2

Embodiment 2 of the present invention will be described. Embodiment 2 is different from Embodiment 1 in the setting of the reference voltage value.

<Apparatus Configuration>

Figure 3:
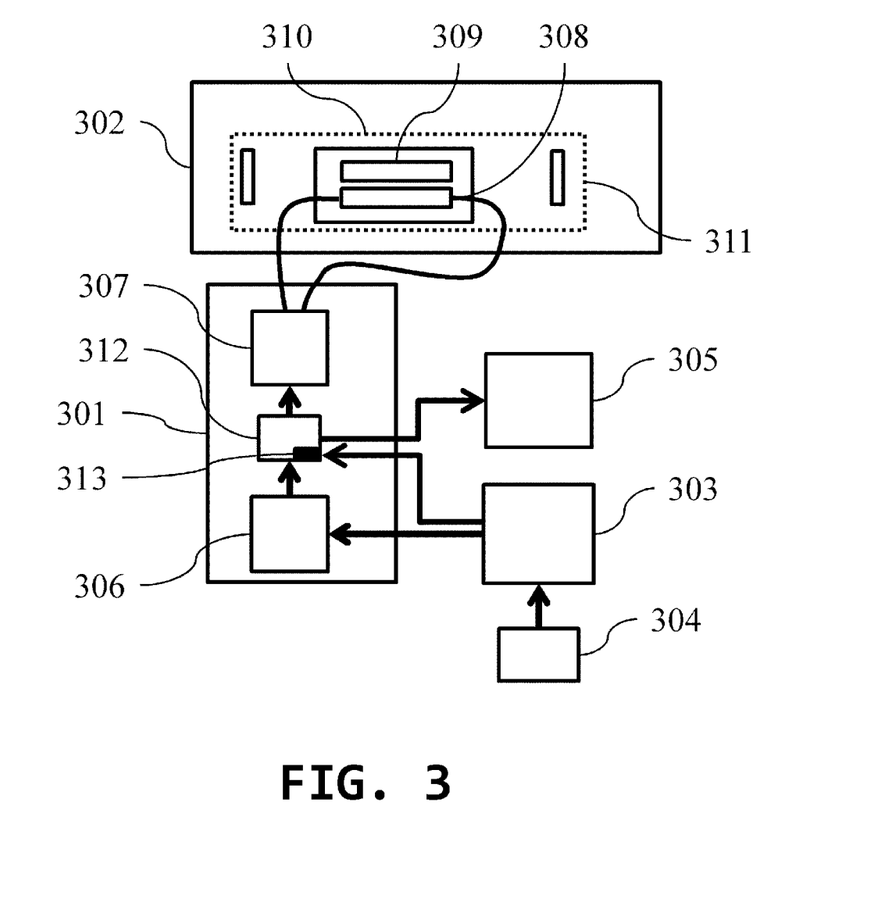
FIG. 3 is a schematic diagram showing an embodiment of the laser apparatus according to the present invention.

Another configuration of the laser apparatus according to the present invention will be described with reference to a schematic diagram in FIG. 3.

A laser apparatus includes a power supplier 301, a laser oscillator 302, a laser controller 303, a laser operator 304, and a display 305.

The power supplier 301 has a voltage supplier 306 and a voltage accumulator 307. A laser oscillator 302 includes an excitation vessel 310 including an excitation source 308 and a laser medium 309, and a resonator 311.

The power supplier 301 has a voltage controller 312 that limits the maximum supplied voltage supplied by the voltage supplier 306. The present invention can be carried out even in a configuration in which the voltage controller 312 is included in the laser controller 303 or operates under the control of the laser controller 303. Furthermore, the voltage controller 312 contains a setting mechanism 313 that sets a reference voltage value. The provision of the setting mechanism 313 enables the reference voltage value to be optionally set.

Furthermore, in this configuration, the display 305 displays a measured voltage value and the reference voltage value.

In a preferred aspect, the setting mechanism 313 predefines the reference voltage value at discrete levels taking the lifetime of the flash lamp into account depending on a time elapsed since the start of use of the flash lamp. For example, an applied voltage is determined which realizes a desired laser output, for example, in an initial state in which the flash lamp starts to be used, and the value of the applied voltage is set to be 130% of a standard value. Then, the maximum supplied voltage is defined at six levels between 105% and 130% of the standard value in accordance with the time elapsed since the start of use.

Setting the range of output adjustment to different levels makes it easier to know a timing at which the flash lamp is to be replaced. The laser apparatus can thus be utilized with no concern for possible unstable output as long as the life of the flash lamp continues. Furthermore, input means may be provided which enables a set value in the setting mechanism to be externally specified or changed.

Embodiment 3

Medical equipment mounted with the laser apparatus according to the present invention is the most preferred embodiment of the invention.

The laser apparatus is applicable to a laser scalpel and a treatment apparatus for aesthetic plastic surgery, skin treatment, and photodynamic therapy (PDT). Moreover, diagnosis apparatuses for photoacoustic diagnosis and measurement being developed are medical equipment suitable for the present invention. The medical equipment needs high power per pulse, and thus, a flash lamp pumped Nd:YAG laser, a flash lamp pumped alexandrite laser, and the like are useful for the medical equipment.

<Apparatus Configuration>

Figure 4:
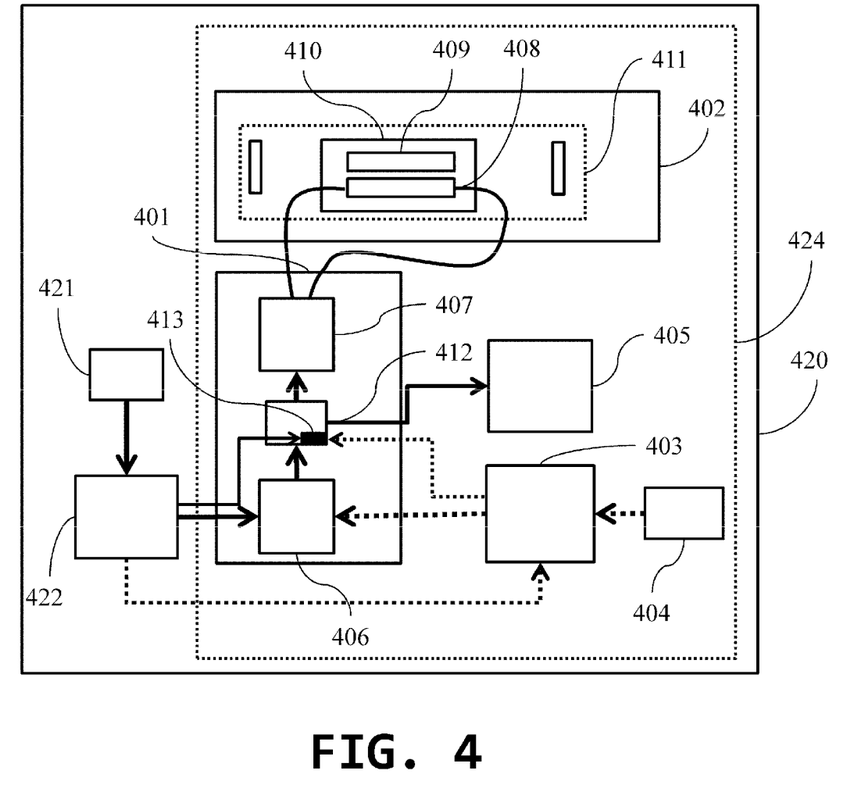
FIG. 4 is a schematic diagram showing an embodiment of medical equipment according to the present invention.

FIG. 4 shows a schematic diagram of a medical apparatus in which the laser apparatus according to the present invention is mounted.

Medical equipment 420 includes an equipment operator 421, an equipment controller 422, and a laser apparatus 424.

Laser oscillation in the laser apparatus 424 is controlled by an equipment operator 421 via the equipment controller 422. The laser apparatus 424 includes a power supplier 401, a laser oscillator 402, a laser controller 403, a laser operator 404, and a display 405.

The power supplier 401 has a voltage supplier 406 and a voltage accumulator 407. The laser oscillator 402 includes an excitation vessel 410 including an excitation source 408 and a laser medium 409, and a resonator 411. Moreover, the power supplier 401 has a voltage controller 412 that limits the maximum supplied voltage supplied by the voltage supplier 406. The voltage controller 412 contains a setting mechanism 413 that sets a reference voltage value.

For laser oscillation, as shown by a solid line, a voltage can be applied to an excitation source 408 by allowing by means of the equipment operator 421 the equipment controller 422 to directly control the power supplier 401 of the laser apparatus 424. Alternatively, as shown by a dotted line, the laser oscillation may be controlled by the equipment controller 422 via the voltage controller 403.

Moreover, a measured voltage value and the reference voltage value can be checked via the display 405 of the laser apparatus 424. In the medical equipment according to Embodiment 3, the equipment controller 422 can set the reference voltage value that defines the maximum voltage supplied to the laser apparatus 424, using the setting mechanism 413.

Embodiment 4

Embodiment 4 of the present invention will be described by focusing on differences from Embodiment 3.

<Apparatus Configuration>

Figure 5:
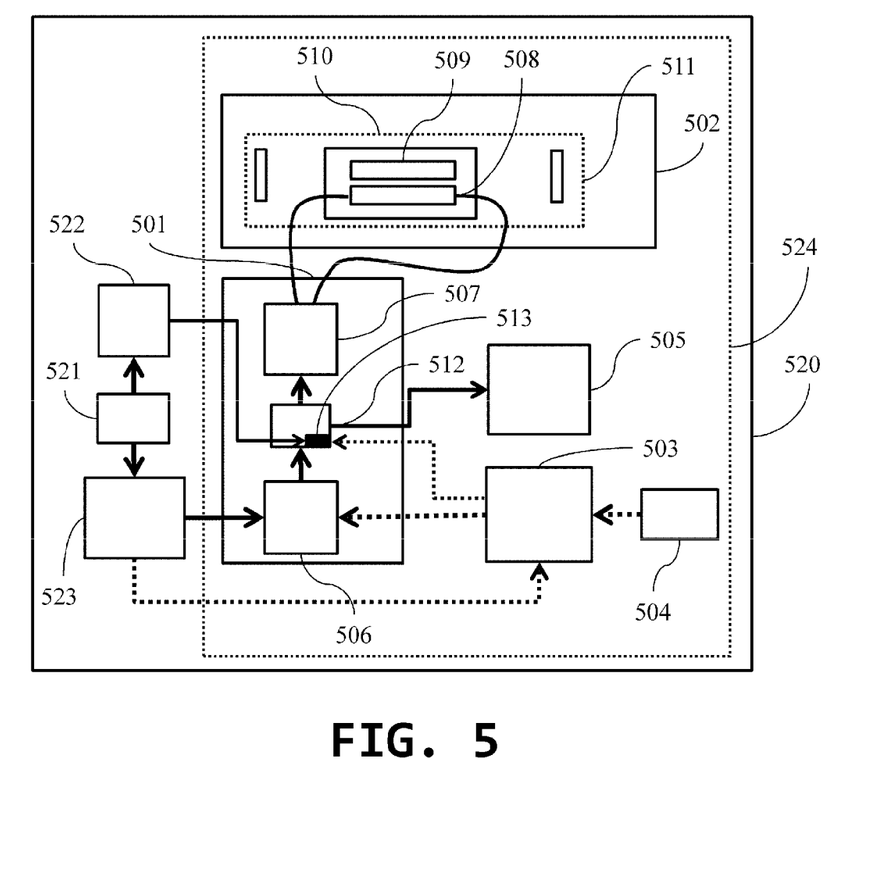
FIG. 5 is a schematic diagram showing an embodiment of the medical equipment according to the present invention.

FIG. 5 shows a schematic diagram of another aspect of the medical apparatus in which the laser apparatus according to the present invention is mounted.

Medical equipment 520 includes an equipment operator 521, two controllers—an equipment A controller 522 and an equipment B controller 523—and a laser apparatus 524.

The laser apparatus 524 includes a power supplier 501, a laser oscillator 502, a laser controller 503, a laser operator 504, and a display 505.

The power supplier 501 has a power supplier 506 and a voltage accumulator 507. The laser oscillator 502 includes an excitation vessel 510 including an excitation source 508 and a laser medium 509, and a resonator 511. Moreover, the power supplier 501 has a voltage controller 512 that limits the maximum supplied voltage supplied by the voltage supplier 506. The voltage controller 512 contains a setting mechanism 513 that sets a reference voltage value. Moreover, a measured voltage value and the reference voltage value can be checked via the display 505 of the laser apparatus 524.

The medical equipment configured according to Embodiment 4 allows the equipment operator 521 to set the reference voltage value that defines the maximum supplied voltage, via the equipment A controller 522 using the setting mechanism 513 of the laser apparatus 524. On the other hand, the medical equipment allows the equipment operator 521 to perform, via the equipment B controller 523, laser control for which the setting mechanism 513 of the laser apparatus 524 is irresponsible.

For laser oscillation, as shown by a solid line, a voltage can be applied to the excitation source 508 by allowing the equipment B controller 523 to directly control the power supplier 501 of the laser apparatus 524. Alternatively, as shown by a dotted line, the laser oscillation may be controlled by the equipment B controller 523 via the laser controller 503.

Moreover, the measured voltage value and the reference voltage value can be checked via the display 505 of the laser apparatus 524.

In the medical equipment, the equipment A controller 522 and the equipment B controller 523 are controllers independent of each other. Utilization conditions for the laser apparatus are set using the equipment A controller 522, and the equipment B controller 523 is used for clinical activities such as treatments and diagnoses. When the reference voltage value need not be changed at the time of clinical activities, the medical equipment is utilized within the range of configuration preset for the configuration according to Embodiment 4. This enables a reduction in considerations for setting changes and erroneous settings and allows clinical activities to be performed under constant conditions.

The maximum allowable laser output energy is defined for a laser scalpel and a treatment apparatus such as a PDT which are configured as described above. This enables a reduction in damage to the segments other than a treatment segment. Furthermore, the laser condition is stabilized to allow the physician to adjust the laser output without anxiety.

Embodiment 5

In a preferred aspect, the configurations shown in FIG. 4 and FIG. 5 are applied to diagnosis apparatuses that perform photoacoustic measurement and the like. A photoacoustic diagnosis apparatus will be described below in brief. Photoacoustic measurement is a measurement technique for irradiating a measurement segment with pulsed laser light of the order of nanoseconds, receiving a photoacoustic wave generated by an absorber that has absorbed light energy, and processing the received signal to form an image.

For example, a technique has been reported in which the photoacoustic diagnosis apparatus is applied to observation of a tumor inside the breast. The periphery of the tumor contains many vascularized tissues with a large absorption coefficient. Hemoglobin contained in blood vessels has an absorption coefficient varying according to an oxidation state. Thus, a method has been proposed in which the state of the tumor is observed by detecting a difference between photoacoustic signals to measure the oxygen saturation of the hemoglobin. Quantitative capability is important for measurement of the oxygen saturation.

The use of a photoacoustic diagnosis apparatus with the laser apparatus according to the present invention mounted therein is expected to keep the output energy of the laser apparatus stable to improve measurement accuracy. Furthermore, the condition of the laser apparatus can be understood to allow the laser apparatus to be constantly utilized in a stable condition.

Example 1

A more specific example of the laser apparatus according to the present invention is illustrated below.

<Apparatus Configuration>

Figure 6:
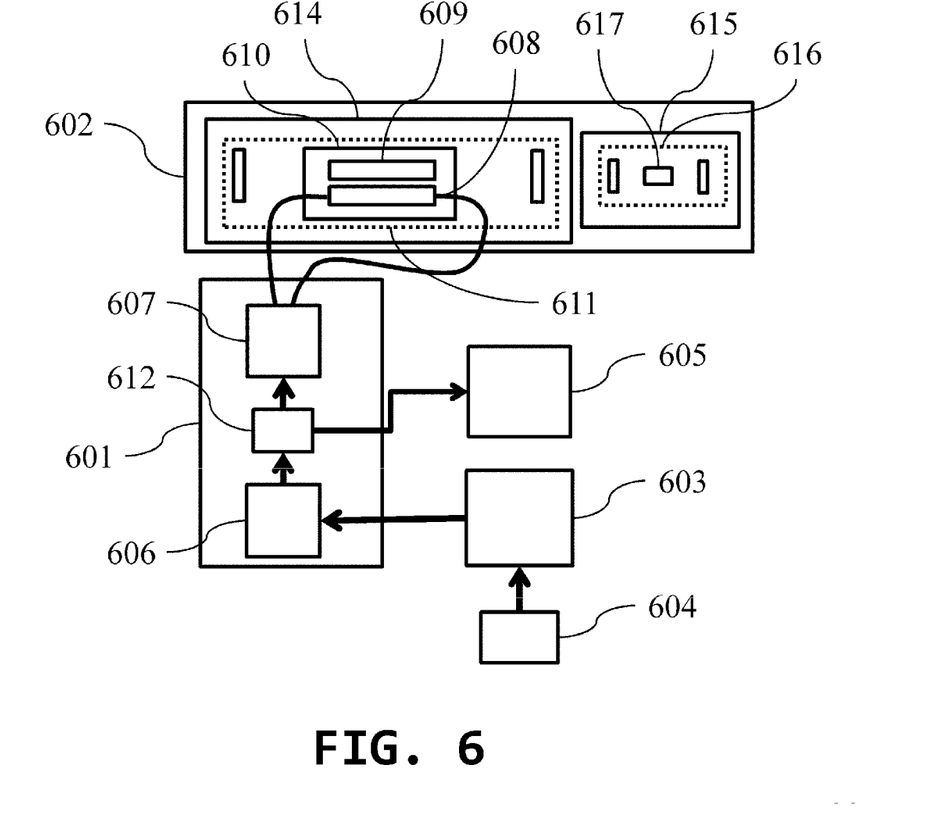
FIG. 6 is a schematic diagram showing an embodiment of the laser apparatus according to the present invention.

FIG. 6 shows a schematic diagram of a Ti:sa laser apparatus according to the present invention. The apparatus includes a power supplier 601, a laser oscillator 602, a laser controller 603, a laser operator 604, a display 605, and a cooling water circulation apparatus (not shown in the drawings).

The laser oscillator 602 includes an Nd:YAG laser 614 serving as an excitation laser and a Ti:sa laser 615.

The Nd:YAG laser 614 includes an excitation vessel 610 and a resonator 611. The excitation vessel 610 includes a flash lamp 608 serving as an excitation source and an Nd:YAG crystal 609 serving as a laser medium. The excitation vessel 610 efficiently condenses light emitted by the flash lamp 608 at the Nd:YAG crystal 609. The resonator 611 includes, as main components, a reflection mirror and an exit mirror arranged across the Nd:YAG crystal and a Q switch (not shown in the drawings) configured to form giant pulses. Furthermore, a nonlinear optical crystal that forms the second harmonic is located outside the resonator and after the exit mirror.

The present invention is applicable to any flash lamp pumped Nd:YAG laser having the above-described basic components and to any second harmonic generation system for the flash lamp pumped Nd:YAG laser, even if the internal details of the laser are not as described above.

The Ti:sa laser 615 includes a resonator 616 and a Ti:sa crystal 617. The Ti:sa crystal 617 is excited using laser light of wavelength 532 nm corresponding to the second harmonic of the Nd:YAG laser, the light serving as excitation light. The light intensity is amplified inside the resonator to oscillate Ti:sa laser light. The Ti:sa laser 615 also includes a wavelength variable mechanism (not shown in the drawings) that selects an oscillation wavelength for Ti:sa, which is capable of oscillating over a wide band. Methods for exciting and amplifying Ti:sa laser light according to the present invention may use various configurations normally used for the Ti:sa laser.

The power supplier 601 includes a voltage supplier 606, a voltage accumulator 607 and a voltage controller 612. Moreover, in Example 1, the power supplier 601 includes a driver for Q switching for the Nd:YAG laser, an igniter or a shimmer component for triggering emission from the flash lamp, and a wavelength selection mechanism for the Ti:sa laser.

The voltage controller 612 directly controls a supplied voltage output by the voltage supplier 606 via a plurality of control steps. Furthermore, a measured voltage value and a reference voltage value formed through by the voltage controller 612 are displayed on the display 605.

During the control steps, first, the measured voltage value is formed. The measured voltage value corresponds to one two-hundredths of the maximum charge voltage provided by the voltage supplier 606, 1,000 V. Then, a comparator circuit including an operational amplifier is used to compare the measured voltage value with the reference voltage value, which defines the maximum allowable value of the supplied voltage. When the measured voltage value is lower than the reference voltage value, a voltage is supplied to the voltage accumulator 607, and electric energy is further applied to the flash lamp 608. On the other hand, when the measured voltage value is equal to or higher than the reference voltage value, application of electric energy to the flash lamp 608 is interrupted.

In the Ti: sa laser apparatus configured according to Example 1, the output intensity of Nd:YAG laser light and its second harmonic is proportional to the value of the voltage supplied by the voltage supplier 606. Furthermore, the output intensity of Ti:sa laser light generated using an excitation laser as an excitation source is proportional to the output intensity of the excitation laser. Hence, the output from the Ti:sa laser depends on the voltage supplied by the voltage supplier 606.

In this case, conversions of energy into flash lamp emission, Nd:YAG laser light, second harmonic laser light, and Ti:sa laser light depend on the condition of the resonator and excitation intensity. Thus, these energy conversions are not always in a constant ratio. Furthermore, near a threshold for laser oscillation with low excitation intensity, the output intensity of the resultant laser light is very unstable.

Thus, the Ti:sa laser apparatus according to the present invention is suitably utilized in an area in which the laser oscillation is stabilized to some degree. However, an available output range can be checked by pre-measuring the relation between the supplied voltage and the intensity of the Ti:sa laser output.

<Measurement Conditions and Results>

In the apparatus in Example 1, the voltage supplier 606 supplies a voltage of 730 V to the voltage accumulator 607. In this state, Ti:sa laser light of wavelength 795 nm was output and measured using an energy measurement instrument installed after a laser output. The value obtained was 100 mJ. At this time, the displayed measured voltage value and reference voltage value were 3.65 V and 3.8 V, respectively. Thus, the rate of the measured voltage value with respect to the reference voltage value is approximately 96%. In Example 1, the laser apparatus was used so that a Ti:sa laser output with wavelength 795 nm constantly contained 100 mJ of energy.

The measured voltage value gradually increases as the apparatus in Example 1 is utilized. When approximately five million pulses from the flash lamp 608 were used, the measured voltage value became equal to the reference voltage value of 3.65 V. Thus, when the measured voltage value and the reference voltage value are displayed while the laser apparatus is in use, the laser condition and the exhaustion level of the lamp can to be understood. Consequently, the laser apparatus was successfully stably used.

Furthermore, when another apparatus was utilized in a similar manner, the measured voltage value became equal to the reference voltage value when two million pulses from the flash lamp were used. When the condition of the resonator inside the apparatus in Example 1 was checked, alignment was found to have changed from its initial state, with the output energy reduced. Thus, the displayed measured voltage value and reference voltage value allowed the laser condition to be understood.

Example 2

As an example of a medical apparatus in which the laser apparatus according to the present invention is mounted, a photoacoustic measurement apparatus will be described. The configuration of the apparatus is the same as the configuration of the medical apparatus illustrated in FIG. 4 described in Embodiment 3.

<Apparatus Configuration>

Medical equipment 420 in Example 2 is a photoacoustic measurement apparatus that is hereinafter referred to as a photoacoustic measurement apparatus 420. Furthermore, a laser apparatus 424 is an alexandrite laser that is hereinafter referred to as an alexandrite laser 424.

The photoacoustic measurement apparatus 420 includes an apparatus operator 421, an apparatus controller 422, and the alexandrite laser 424. Although not shown in FIG. 4, the photoacoustic measurement apparatus 420 has a laser irradiator of the alexandrite laser 424, an ultrasonic receiver that detects a photoacoustic wave resulting from laser irradiation. The photoacoustic measurement apparatus 420 further has a signal processor and a signal converter which execute processing such as amplification and digital conversion on a measured photoacoustic wave, whereby a photoacoustic signal is generated. The photoacoustic measurement apparatus 420 also has a constructor that acquires characteristic information on the inside of the object from the photoacoustic signal using a known image reconstruction technique and an image display that displays an image of the inside of the object based on the characteristic information (neither of the constructor and the image display are shown in the drawings).

The alexandrite laser 424 includes a power supplier 401, a laser oscillator 402, a laser controller 403, a laser operator 404, a display 405, and a cooling water circulation apparatus. The laser oscillator 402 includes an excitation vessel 410 and a resonator 411. The excitation vessel 410 includes a flash lamp serving as an excitation source 408 and an alexandrite crystal serving as a laser medium 409. The flash lamp and the alexandrite crystal are hereinafter referred to as the flash lamp 408 and the alexandrite crystal 409, respectively. The excitation vessel 410 is configured such that light emitted by the flash lamp 408 is efficiently condensed at the alexandrite crystal 409.

The resonator 411 includes, as main components, a reflection mirror and an exit mirror arranged across the alexandrite crystal and a Q switch configured to form giant pulses, and a wavelength selection mechanism that selects an oscillation wavelength.

The present invention is applicable to any flash lamp pumped alexandrite laser system having the above-described basic components even if the internal details of the laser are not as described above.

The power supplier 401 includes a voltage supplier 406, a voltage accumulator 407, a voltage controller 412, and a setting mechanism 413. Moreover, the power supplier 401 includes a driver for Q switching for the alexandrite laser 424, an igniter or a shimmer component for triggering emission from the flash lamp, and a wavelength selection mechanism.

The voltage controller 412 directly controls a supplied voltage output by the voltage supplier 406 via a plurality of control steps. Furthermore, a measured voltage value and a reference voltage value formed through the voltage controller 412 are displayed on the display 405. Moreover, the reference voltage value can be changed using the setting mechanism 413. The setting change in the setting mechanism 413 can performed not only by the laser operator 404 via the voltage controller 403 but also by an operation performed by the apparatus operator 421 of the photoacoustic measurement apparatus 420, via the apparatus controller 422.

During the control steps, first, the measured voltage value is formed. The measured voltage value corresponds to one two-hundredths of the maximum charge voltage provided by the voltage supplier 406, 1,500 V. Then, a comparator circuit including an operational amplifier is used to compare the measured voltage value with the reference voltage value, which defines the maximum allowable value of the supplied voltage. When the measured voltage value is lower than the reference voltage value, a voltage is supplied to the voltage accumulator 407, and electric energy is further applied to the flash lamp 408. On the other hand, when the measured voltage value is equal to or higher than the reference voltage value, application of electric energy to the flash lamp 408 is interrupted.

The output intensity of the alexandrite laser 424 configured according to Example 2 depends on the value of the voltage supplied by the voltage supplier 406.

In this case, the energy conversion efficiency of output light from the alexandrite laser relative to flash lamp illumination depends on the resonator condition and the excitation intensity. Thus, the energy conversion is not always in a constant ratio. An available output range can be checked by pre-measuring the relation between the supplied voltage and the intensity of the alexandrite laser output in a stable state.

<Measurement Conditions and Results>

In the apparatus in Example 2, the voltage supplier 406 supplies a voltage of 1,000 V to the voltage accumulator 407. In this state, alexandrite laser light of wavelength 755 nm was output and measured using an energy measurement instrument installed after the laser output. The value obtained was 200 mJ. At this time, the measured voltage value and the reference voltage value were 5.0 V and 5.25 V, respectively. Thus, the rate of the measured voltage value with respect to the reference voltage value is approximately 95%. In Example 2, the laser apparatus was used so that an alexandrite laser output with wavelength 755 nm constantly contained 200 mJ of energy.

The measured voltage value gradually increased as more pulses from the apparatus in Example 1 were utilized. When approximately five million pulses from the flash lamp 408 were used, the measured voltage value became equal to the reference voltage value of 5.25 V. Moreover, the apparatus operator 421 was allowed to change the reference voltage value to 5.55 V via the apparatus controller 422 using the setting mechanism 413. Then, the laser continued to be used in the above-described state. When a total of 7.5 million pulses from the laser were used, the measured voltage value became equal to the changed reference voltage value of 5.55V. Thus, when the measured voltage value and the reference voltage value are displayed while the laser apparatus is in use, the laser condition and the exhaustion level of the lamp can be understood. Consequently, the laser apparatus was successfully stably used.

A photoacoustic wave from a phantom that is a pseudo living body was received using an ultrasound measurement instrument in the photoacoustic measurement apparatus 420. When the alexandrite laser output with wavelength 755 nm was adjusted to 200 mJ, the supplied voltage was 1,030 V and the measured voltage value was 5.15 V because the alexandrite laser was not at thermal equilibrium. The reference voltage value was adjusted to 5.50 V.

In this state, the supplied voltage from the voltage supplier 406 was adjusted so that the alexandrite laser constantly provided 200 mJ of output. Then, the measured voltage value approached the neighborhood of 5.00 V as the measured time elapsed.

On the other hand, when the apparatus was used without apparatus warm-up, an increase in the supplied voltage from the voltage supplier 406 to 105 V or higher caused the interruption of electric energy application to the flash lamp 408, resulting in stop of the laser oscillation. That is, the laser oscillation stopped because the apparatus condition was unstable, making the measured voltage value equal to the reference voltage value of 5.50 V.

As described above, the application of the present invention allows avoidance of photoacoustic measurement in the state where the apparatus is unstable. Furthermore, the condition of the laser apparatus can be understood, enabling the laser apparatus to be utilized in a stable state.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-162941, filed on Aug. 6, 2013, which is hereby incorporated by reference herein in its entirety.

What is claimed is:

1. An object information acquiring apparatus comprising:
a laser medium that oscillates laser light;
an excitation source that excites the laser medium;
a voltage accumulator that applies a voltage to the excitation source;
a voltage supplier that supplies a voltage to the voltage accumulator;
a voltage controller that limits a maximum supplied voltage from the voltage supplier;
a receiver that receives a photoacoustic wave generated by an object irradiated with the laser light; and
a constructor that acquires characteristic information relating to the object in use of the photoacoustic wave,
wherein the voltage controller compares a measured voltage value obtained by implementing division of a supplied voltage from the voltage supplier with a reference voltage value defining the maximum supplied voltage.

2. The object information acquiring apparatus according to claim 1, further comprising a display that displays a result of the comparison performed by the voltage controller.

3. The object information acquiring apparatus according to claim 1, wherein a result of the comparison performed by the voltage controller is a ratio of the measured voltage value to the reference voltage value.

4. The object information acquiring apparatus according to claim 3, wherein the voltage supplier supplies a voltage such that the ratio of the measured voltage value to the reference voltage value is lower than 100% and equal to or more than 90%.

5. The object information acquiring apparatus according to claim 1, further comprising a setting mechanism that sets the reference voltage value.

6. The object information acquiring apparatus according to claim 5, wherein the setting mechanism specifies the reference voltage value at different levels according to a time elapsed since start of using the excitation source.

7. The object information acquiring apparatus according to claim 6, wherein the excitation source is a flash lamp.

8. The object information acquiring apparatus according to claim 1, further comprising a wavelength selector for the laser light to be oscillated,
wherein the constructor acquires an oxygen saturation in the object in use of characteristic information on a plurality of wavelengths.

9. A laser apparatus comprising:
a laser medium that oscillates laser light;
an excitation source that excites the laser medium;
a voltage accumulator that applies a voltage to the excitation source;
a voltage supplier that supplies a voltage to the voltage accumulator; and
a voltage controller that limits a maximum supplied voltage from the voltage supplier;
wherein the voltage controller compares a measured voltage value obtained by implementing division of a supplied voltage from the voltage supplier with a reference voltage value defining the maximum supplied voltage prior to an oscillation of laser light, and the voltage controller controls based on a result of the comparison, the voltage supplier to supply a voltage to the voltage accumulator.

10. A medical apparatus comprising:
the laser apparatus according to claim 9;
an irradiator that irradiates an object with oscillated laser light; and
an equipment controller that controls the laser apparatus and the irradiator based on a result of a comparison performed by the voltage controller.

11. An object information acquiring apparatus comprising:
a laser medium that oscillates laser light;
an excitation source that excites the laser medium;
a voltage accumulator that applies a voltage to the excitation source;
a voltage supplier that supplies a voltage to the voltage accumulator;
a voltage controller that limits a supplied voltage from the voltage supplier;
a receiver that receives a photoacoustic wave generated by an object irradiated with the laser light; and
a constructor that acquires characteristic information relating to the object in use of the photoacoustic wave,
wherein the voltage controller compares a measured voltage value obtained by implementing division of a supplied voltage from the voltage supplier with a reference voltage value.

12. The object information acquiring apparatus according to claim 11, further comprising a display that displays a result of the comparison performed by the voltage controller.

13. The object information acquiring apparatus according to claim 11, wherein a result of the comparison performed by the voltage controller is a ratio of the measured voltage value to the reference voltage value.

14. The object information acquiring apparatus according to claim 13, wherein the voltage supplier supplies a voltage such that the ratio of the measured voltage value to the reference voltage value is lower than 100% and equal to or more than 90%.

15. The object information acquiring apparatus according to claim 11, further comprising a setting mechanism that sets the reference voltage value.

16. The object information acquiring apparatus according to claim 15, wherein the setting mechanism specifies the reference voltage value at different levels according to a time elapsed since start of using the excitation source.

17. The object information acquiring apparatus according to claim 16, wherein the excitation source is a flash lamp.

18. The object information acquiring apparatus according to claim 11, further comprising a wavelength selector for the laser light to be oscillated,
wherein the constructor acquires an oxygen saturation in the object in use of characteristic information on a plurality of wavelengths.

19. The object information acquiring apparatus according to claim 1, wherein the voltage controller compares the measured voltage value obtained by implementing division of a supplied voltage from the voltage supplier with the reference voltage value defining the maximum supplied voltage prior to an oscillation of laser light, and the voltage controller controls based on a result of the comparison, the voltage supplier to supply a voltage to the voltage accumulator.

20. The object information acquiring apparatus according to claim 11, wherein the voltage controller compares the measured voltage value obtained by implementing division of a supplied voltage from the voltage supplier with the reference voltage value defining the maximum supplied voltage prior to an oscillation of laser light, and the voltage controller controls based on a result of the comparison, the voltage supplier to supply a voltage to the voltage accumulator.

* * * * *